(12) United States Patent
Karp et al.

(10) Patent No.: US 7,381,958 B2
(45) Date of Patent: Jun. 3, 2008

(54) LANTHANUM HALIDE SCINTILLATORS FOR TIME-OF-FLIGHT 3-D PET

(75) Inventors: Joel S. Karp, Glenside, PA (US); Suleman Surti, Philadelphia, PA (US)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 74 days.

(21) Appl. No.: 10/706,799

(22) Filed: Nov. 12, 2003

(65) Prior Publication Data

US 2008/0099685 A1    May 1, 2008

Related U.S. Application Data

(60) Provisional application No. 60/425,511, filed on Nov. 12, 2002.

(51) Int. Cl.
   *G01T 1/164* (2006.01)
(52) U.S. Cl. ............................................... 250/363.03
(58) Field of Classification Search ............ 260/363.03
   See application file for complete search history.

(56) References Cited

U.S. PATENT DOCUMENTS

| | | | |
|---|---|---|---|
| 4,559,597 A * | 12/1985 | Mullani | 600/407 |
| 4,743,764 A * | 5/1988 | Casey et al. | 250/363.03 |
| 4,980,552 A * | 12/1990 | Cho et al. | 250/363.03 |
| 5,015,860 A | 5/1991 | Moses | 250/361 |
| 5,210,420 A * | 5/1993 | Hartz et al. | 250/363.03 |

(Continued)

FOREIGN PATENT DOCUMENTS

WO    WO 0160944 A2  *  8/2001

(Continued)

OTHER PUBLICATIONS

Van Loef et al., High Energy Resolution Scintillator: Ce+3 Activated LaBr3, Sep. 3, 2001, Applied Physics Letters, vol. 79, pp. 1573-1574.*

(Continued)

*Primary Examiner*—Christine Sung
(74) *Attorney, Agent, or Firm*—Woodcock Washburn LLP

(57) ABSTRACT

A Lanthanum Halide scintillator (for example $LaCl_3$ and $LaBr_3$) with fast decay time and good timing resolution, as well as high light output and good energy resolution, is used in the design of a PET scanner. The PET scanner includes a cavity for accepting a patient and a plurality of PET detector modules arranged in an approximately cylindrical configuration about the cavity. Each PET detector includes a Lanthanum Halide scintillator having a plurality of Lanthanum Halide crystals, a light guide, and a plurality of photomultiplier tubes arranged respectively peripherally around the cavity. The good timing resolution enables a time-of-flight (TOF) PET scanner to be developed that exhibits a reduction in noise propagation during image reconstruction and a gain in the signal-to-noise ratio. Such a PET scanner includes a time stamp circuit that records the time of receipt of gamma rays by respective PET detectors and provides timing data outputs that are provided to a processor that, in turn, calculates time-of-flight (TOF) of gamma rays through a patient in the cavity and uses the TOF of gamma rays in the reconstruction of images of the patient.

5 Claims, 7 Drawing Sheets

U.S. PATENT DOCUMENTS

| | | | |
|---|---|---|---|
| 5,453,623 A * | 9/1995 | Wong et al. | 250/363.03 |
| 6,285,028 B1 | 9/2001 | Yamakawa | 250/370.09 |
| 6,297,506 B1 * | 10/2001 | Young et al. | 250/369 |
| 6,362,479 B1 * | 3/2002 | Andreaco et al. | 250/366 |
| 6,373,059 B1 * | 4/2002 | Stearns et al. | 250/363.03 |
| 6,552,348 B2 * | 4/2003 | Cherry et al. | 250/363.03 |
| 2004/0017224 A1 | 1/2004 | Tumer et al. | 327/51 |
| 2004/0238474 A1 * | 12/2004 | Heinisch et al. | 213/75 R |
| 2005/0006589 A1 * | 1/2005 | Joung et al. | 250/370.09 |
| 2005/0082484 A1 * | 4/2005 | Srivastava et al. | 250/361 R |
| 2005/0104001 A1 * | 5/2005 | Shah | 250/363.03 |
| 2005/0104002 A1 * | 5/2005 | Shah | 250/363.03 |

FOREIGN PATENT DOCUMENTS

| | | | |
|---|---|---|---|
| WO | WO 0160945 A2 * | 8/2001 | |
| WO | WO 2004044613 A2 * | 5/2004 | |

OTHER PUBLICATIONS

Van Loef et al., High Energy Resolution Scintillator: Ce+3 Activated LaCl3, Sep. 4, 2000, Applied Physics Letters, vol. 77, pp. 1467-1468.*

Guillot Novel et al., Optical and Scintillation Properties of Cerium Doped LaCl3, LuBr3, and LuCl3, 1999, Journal of Luminescence, vol. 85, 21-35.*

Accorsi, R., et al., "Optimization of a fully 3D single scatter simulation algorithm for 3D PET," *Physics in Med. & Biol.*, 2004, 49, 2577-2598.

Adam, L.-E., et al., "Performance of a whole-body PET scanner using curve-plate NaI(T1) detectors," *J. Nucl. Med.*, 2001, 42, 1821-1830.

Allemand, R., et al., "Potential advantages of a cesium fluoride scintillator for a time-of-flight positron camera," *J. Nucl. Med.*, 1980, 21, 153-155.

Bendrieum, B., et al. "A technique for the correction of scattered radiation in a PET system using time-of-flight information," *J. of Computer Assisted Tomography*, 1986, 10(2), 287-295.

Budinger, T.F., "Time-of-flight positron emission tomography: status relative to conventional PET," *J. Nucl. Med.*, 1983, 24(1), 73-78.

Casey, M.E., et al., "A multicrystal two dimensional BGO detector system for positron emission tomography," *IEEE Transactions on Nuclear Science*, 1986, 33(1), 460-463.

Cherry, S.R., et al., "A comparison of PET detector modules employing rectangular and round photomultiplier tubes," *IEEE Transactions on Nuclear Science*, 1995, 42(4), 1064-1068.

Daube-Witherspoon, M.E., et al., "An iterative image space reconstruction algorithm suitable for volume ECT," *IEEE Transactions on Medical Imaging*, 1986, MI-5(2), 61-66.

Daube-Witherspoon, M.E., et al., "Application of the row action maximum likelihood algorithm with spherical basis functions to clinical PET imaging," *IEEE Transactions on Nuclear Science*, 2001, 48(1), 24-30.

Freifelder, R., et al., "Design and performance of the Head Penn-Pet scanner," *IEEE Transactions on Nuclear Science*, 1994, 41(4), 1436-1440.

Haynor, D.R., et al., "A scheme for accidental coincidence correction in time-of-flight positron tomography: theory and implementation," *IEEE Transactions on Nuclear Science*, 1988, 35(1), 753-756.

Ishibashi, H., et al., "Cerium doped GSO scintillators and its application to position sensitive detectors," *IEEE Trans. Nucl. Sci.*, 1989, 36(1), 170-172.

Karp, J.S., et al., "Performance of a position-sensitive scintillation detector," *Phys. Med. Biol.*, 30(7), 1985, 643-655.

Karp, J.S., "Singles transmission in volume imaging PET with a $^{137}Cs$ source," *Phys. Med. Biol.*, 1995, 40, 929-944.

Karp, J.S., et al., "Performance of a brain PET camera based on anger-logic gadolinium oxyorthosilicate detectors," *J. of Nuclear Med.*, 2003, 44(8), 1340-1349.

Karp, J.S., et al., "Three-dimensional imaging characteristics of the Head Penn-Pet scanner," *J. of Nuclear Med.*, 1997, 38(4), 636-643.

Karp, J.S., et al., "Data processing and image reconstruction methods for the Head Penn-Pet scanner," *IEEE Transactions on Nuclear Science*, 1998, 45(3), 1144-1151.

Karp, J.S., et al., "Continuous-slice Penn-Pet: a positron tomography with vlume imaging capability," *J. Nucl. Med.*, 1990, 31, 617-627.

Karp, J.S., et al., "Event localization in a continuous scintillation detector using digital processing," *IEEE, TNS*, 1986, 1-5.

Karp, J.S., "Is LSO the future of PET?," *Eur. J. of Nucl. Med.*, 2002, 29, 1523-1525.

Kimdon, J.A., et al., "Effect of random and scatter fractions in variance reduction using time-of-flight information," Conference Record of the 2003 *IEEE Nuclear Science Symposium and Medical Imaging Conference*, 2003, 3 pages.

Kuhn, A., et al., "Design of a lanthanum bromide detector for TOF PET," *IEEE Trans. Nucl. Sci.* (accepted for publication), 2004, 6 pages.

Lewellen, T.K., et al., "Improving the performance of the SP-3000 PET detector modules," *IEEE Transactions on Nuclear Science*, 1992, 39(4), 1074-1078.

Lewellen, T.K., et al., "An experimental evaluation of the effect of time-of-flight information in image reconstructions for the scanditronix/PETT electronics SP-3000 positron emission tomography—preliminary results," *IEEE Transactions on Nuclear Science*, 1989, 36(1), 1095-1099.

Lewellen, T.K., "Time-of-flight PET," *Seminars in Nuclear Med.*, 1998, XXVIII(3), 268-275.

Mankoff, D.A., et al., "The high count rate performance of a two-dimensionally position-sensitive detector for positron emission tomography," *Phys. Med. Biol.*, 1989, 34(4), 437-456.

Mazoyer, B., et al., "Physical characteristics of TTV03, a new high spatial resolution time-of-flight positron tomography," *IEEE Transactions on Nuclear Science*, 1990, 37(2), 778-782.

Melcher, C.L., et al., "Cerium-doped lutetium oxyorthosilicate: a fast, efficient new scintillator," *IEEE Trans. Nucl. Sci.*, 1992, 39, 502-505.

Melcher, C.L., et al., "Scintillation properties of LSO:Ce boules," *IEEE Trans. Nucl. Sci.*, 2000, 47, 965-968.

Moses, W.W., et al., "Time of flight in PET revisited," *IEEE Transactions on Nuclear Science*, 2003, 50(5), 1325-1330.

Moses, W.W., et al., "Prospects for time-of-flight PET using LSO scintillator," *IEEE Transactions on Nuclear Science*, 1999, NS-46, 474-478.

Moses, W.W., "Current trends in scintillator detectors and materials," *Nuclear Instruments and Methods in Physics Research A*, 2002, 487, 123-128.

Moszyński, M., et al., "Energy resolution of scintillation detectors readout with large avalanche photodiodes and photomultipliers," *IEEE Trans. Nucl. Sci.*, 1998, 45, 472-477.

Moszyński, M., et al., "Further study of scintillation counters with $BaF_2$ crystals for time-of-flight positron tomography in medicine," *Nucl. Instru. Meth.*, 1984, A226, 534-541.

Moszyński, M., et al., "Recent progress in fast timing with CsF scintillators in application to time-of-flight positron tomography in medicine," *Nucl. Instru. Meth.*, 1983, 205, 239-249.

Moszyński, M., "Timing properties of GSO, LSO and other Ce doped scintillators," *Nuclear Instruments and Methods in Physics Research*, 1996, 372, 51-58.

Moszyński, M., "Inorganic scintillation detectors in γray spectrometry," *Nuclear Instruments and Methods in Physics Research*, 2003, 505, 101-110.

Mullani, N.A., et al., "Feasibility of time-of-flight reconstruction in positron emisson tomography," *J. Nucl. Med.*, 1980, 21, 1095-1097.

Mullani, N.A., et al., "Preliminary results with toppet," *IEEE Transactions on Nuclear Science*, 1983, NS-30(1), 739-743.

Parra, L., et al., "List-mode likelihood: EM algorithm and image quality estimation demonstrated on 2-D PET," *IEEE Transactions on Medical Imaging*, 1998, 17(2), 228-235.

Perkins, AE., et al., "Performance measurements of a pixilated NaI(T1) PET scanner," *IEEE Transactions on Nuclear Science*, 2003, 50(3), 373-377.

Philippe, E.A., "Some signal processing aspects of time-of-flight positron emission tomography (TOFPET) system implementation," *IEEE Trans. Nucl. Sci.*, 1983, 30, 715-719.

Philippe, E.A., et al., "Real-time image reconstruction for time-of-flight positron emission tomography (TOPPET)," *IEEE Transactions on Nuclear Science*, 1982, NS-29, 524-528.

Politte, D.G., "Results of a comparative study of a reconstruction procedure for producing improved estimates of radioactivity distributions in time-of-flight emission tomography," *IEEE Transactions on Nuclear Science*, 1984, NS-31(1), 614-619.

Reader, A.J., "Fast accurate iterative reconstruction for low-statistics positron volume imaging," *Phys. Med. Biol.*, 1998, 43, 835-846.

Robeson, W., et al., "Superpett 3000 time-of-flight pet tomography: optimization of factors affecting quantitation," *IEEE Transactions on Nuclear Science*, 1993, 40(2), 135-142.

Shah, K.S., et al., "$LaBr_3$:Ce scintallators for gamma-ray spectroscopy," *IEEE Transactions on Nuclear Science*, 2003, 50(6), 241-2413.

Shah, K.S., et al., "$LaCl_3$:Ce scintillator for $\gamma$-ray detection," *Nuclear Instruments and Methods in Physics Research*, 2003, 505, 76-81.

Snyder, D.L., et al., "A mathematical model for positron emission tomography system having time-of-flight measurements," *IEEE Trans. Nucl. Sci.*, 1981, 28, 3575-3585.

Snyder D.L., et al., "Some noise camparisons of data-collection arrays for emission tomography-systems having time-of-flight measurements," *IEEE Transactions on Nuclear Science*, 1982, NS-29(1), 1029-1033.

Soussaline, F., et al., "New developments in positron emission tomography instrumentation using the time-of-flight information," in The Metabolism of the Human Brain Studied with Positron Emission Tomography, Greitz, T., et al., (Eds.), Raven Press, New York, 1985, 1-12.

Surti, S., et al., "Optimizing the performance of a PET detector using discrete GSO crystals on a continuous light guide," *IEEE Trans. Nucl. Sci.*, 2000, 47, 1030-1036.

Surti, S., et al., "Imaging characteristics of a 3-dimensional GSO whole-body PET camera," *J. of Nuclear Medicine*, 2004, 45(6), 1040-1049.

Surti, S., et al., "Design evaluation of A-PET: a high sensitivity animal PET camera," *IEEE Transactions on Nuclear Science*, 2003, 50(5), 1357-1363.

Surti, S., et al., "Slotted surface treatment of position-sensitive NaI(T1) detectors to improve detector performance," *IEEE Transactions on Nuclear Science*, 2001, 48(6), 2418-2423.

Surti, S., et al., "Evaluation of pixilated NaI(T1) detectors for PET," *IEEE Transactions on Nuclear Science*, 2003, 50(1), 24-31.

Surti, S., et al., "Image quality assessment of $LaBr_3$ based 3D PET scanners," *Phys. Med. Biol.* (accepted for publication), 2004, 1-25.

Surti, S., et al., "Investigation of lanthanum scintillators for 3-D PET," *IEEE Transactions on Nuclear Science*, 2003, 50(3), 348-354.

Ter-Pogossian, M.M., et al., "Super PETT I: A positron emission tomography utilizing photon time-of-flight information," *IEEE Transactions on Medical Imaging*, 1982, MI-1(3), 179-187.

Tomitani, T., "Image reconstruction and noise evaluation in photon time-of-flight assisted positron emission tomography," *IEEE Trans. Nucl. Sci.*, 1981, 28, 4582-4589.

van Eijk, C.W.E., "Inorganic scintillators in medical imaging," *Phys. Med. Biol.*, 1989, 47, R85-R106.

van Loef, E.V.D., et al., "High-energy-resolution scintillator: $Ce^{3+}$ activated $LaCl_3$," *Appl. Phys. Letts.*, 77(10), 1467-1468.

van Loef, E.V.D., et al., "High-energy-resolution scintillator: $Ce^{3+}$ activated $LaBr_3$," *Appl. Phys. Letts.*, 2001, 79(10), 1573-1575.

Wong, W.-H., et al., "An analog decoding BGO block detector using circular photomultipliers," *Transactions on Nuclear Science*, 1995, 42(4), 1095-1101.

Wong, W.-H., et al., "Image improvement and design optimization of the time-of-flight PET," *J. of Nuclear Medicine*, 1983, 24, 52-60.

Wong, W.-H., et al., "Characteristics of small barium fluoride ($BaF_2$) scintillator for high intrinsic resolution time-of-flight positron emission tomography," *IEEE Transactions on Nuclear Science*, 1984, NS-31(1), 381-386.

Yamamoto, M., et al., "Effects of the software coincidence timing window in time-of-flight assisted positron emission tomography," *IEEE Transactions on Nuclear Science*, 1983, NS-30(1), 711-714.

Yamamoto, M., et al., "Time-of-flight positron imaging and the resolution improvement by an iterative method," *IEEE Transactions on Nuclear Science*, 1989, 36(1), 998-1002.

Yamamoto, M., et al., "Experimental assessment of the gain achieved by the utilization of time-of-flight information in a positron emission tomography (Super PETT1)," *IEEE Transactions on Medical Imaging*, 1982, MI-1(3), 187-192.

Yamaya, T., et al., "High-resolution image reconstruction method for time-of-flight positron emission tomography," *Phys. Med. Biol.*, 2000, 45, 3125-3134.

Ziegler, S.I., et al., "Effects of scintillation light collection on the time resolution of a time-of-flight detector for annihilation quanta," *IEEE Transactions on Nuclear Science*, 1990, 37(2), 574-579.

The PCT International Search Report dated Apr. 28, 2004 (PCT/US03/35922).

* cited by examiner

Summed 1D profile

LANTHANUM HALIDE SCINTILLATORS FOR TIME-OF-FLIGHT 3-D PET

CROSS REFERENCE TO RELATED APPLICATIONS

This application claims benefit to U.S. Provisional Application No. 60/425,511 filed Nov. 12, 2002.

GOVERNMENT SUPPORT

The present invention was supported by the U.S. Department of Energy under Grant No. DOE DE-FG02-88ER60642 and by the National Institutes of Health under NIH Grant No. 1-R21-EB-001684-01. The government may have certain rights in the invention.

FIELD OF THE INVENTION

The present invention relates to the use of Lanthanum Halide scintillators (e.g., $LaBr_3$) for three-dimensional Positron Emission Tomography (PET) so as to enable measurement of time-of-flight (TOF) information.

DESCRIPTION OF THE PRIOR ART

As the need in clinical PET has grown recently, there is an increased demand for higher performance (better image quality). Improved lesion detection is the major goal for oncology studies—it is critical that small lesions are not missed. The present inventors have demonstrated with current scanners based on Gadolinium Oxyorthosilicate (GSO) that excellent image quality in 3-D is achieved with fast scintillators that also have good energy resolution. Lanthanum Halide scintillators, in particular $LaBr_3$, are faster than GSO and have much better energy resolution—in fact their energy resolution is better than Sodium Iodide, NaI(Tl), which has long been the gold standard. The present inventors have concluded that 3-D imaging for clinical PET is ultimately limited by randoms and, especially for heavy patients, the combination of scatter and randoms. Thus, even with somewhat lower stopping power than GSO, the present inventors believe that a PET scanner with $LaBr_3$ will achieve much higher performance for clinical whole-body studies. However, no $LaBr_3$ PET scanner is described in the literature.

There has been considerable research and development of inorganic scintillators for PET imaging over the past several decades [C. W. E. van Eijk, Inorganic scintillators in medical imaging, Phys. Med. Biol. 47: R85-R106, 1989] and the search for the ideal scintillator seems to be intensifying. The ideal scintillator has high light output (and energy resolution), high stopping power, and fast decay time. Although far from ideal, both NaI(Tl) and Bismuth Germanate (BGO) have been used in PET for a long period of time—almost 30-years for NaI(Tl) and 20 years for BGO—and both continue to be incorporated in commercial PET instruments capable of high performance. Nevertheless, LSO and GSO have drawn much attention recently, as both lead to higher performance for 3-D instruments. While LSO is relatively new [Melcher C L, Schweitzer J S, Cerium-doped lutetium oxyorthosilicate: a fast, efficient new scintillator, IEEE Trans. Nucl. Sci. 39: 502-505, 1992], GSO has been available for awhile [K. Takagi and T. Fukazawa, Cerium-activated Gd2SiO5 single crystal scintillator, App Phys Lett 42: 43-45, 1983; H. Ishibashi, K. Shimizu, and K. Susa, Cerium Doped GSO Scintillators and its Application to Position Sensitive Detectors, IEEE Trans. Nucl. Sci. 36: 170-172, 1989]. GSO had been largely ignored until recently since it does not offer an obvious advantage over BGO for 2-D instruments, but it has a very favorable combination of properties that make it an excellent scintillator for 3-D instruments.

One drawback with both LSO and GSO is the high cost of these scintillators—at least a factor of 5-10 higher than NaI(Tl) and a factor of 3-6 higher than BGO. It is unlikely that either LSO or GSO will reach the low cost of NaI(Tl) and BGO, due to the higher melting point and difficulty in growing large boules. Also, it is not certain that growth of LSO will improve and overcome the problems of inhomogeneous light output and decay time. The inhomogeneous light output [C. L. Melcher, M. Schmand M, et al., Scintillation properties of LSO:Ce boules, IEEE Trans. Nucl. Sci. 47: 965-968, 2000] and the intrinsic non-proportionality of light conversion of LSO lead to poorer energy resolution than for GSO, even though GSO has lower light output [M. Moszynski, M. Kapusta, D. Wolski, et. al., Energy resolution of scintillation detectors readout with large avalanche photodiodes and photomultipliers. IEEE Trans. Nucl. Sci. 45: 472-477, 1998]. One reason why GSO is favored over LSO by the present inventors is because of the more uniform light output and better energy resolution, which the inventors feel is important for 3-D imaging. Also, GSO is lower cost than LSO for many applications and is not radioactive so it allows the use of singles transmission scanning [Karp J S, Muehllehner G, Qu H e, Yan X H, Singles transmission in volume imaging PET with a 137Cs source, Phys Med Biol 40: 929-944, 1995] and is insensitive to temperature variations [C. L. Melcher, J. S. Schweitzer, R. A. Manent&, C. A. Peterson, Applicability of GSO scintillators for well logging, IEEE Trans. Nucl. Sci. 38: 506-509, 1991].

TABLE 1

Comparison of properties of scintillators for PET. Energy resolution taken at 662 keV.

| Scintillator | NaI (Tl) | BGO | GSO | LSO | CsF | BaF2 | LaCl3 | LaBr3 |
|---|---|---|---|---|---|---|---|---|
| $\tau$ (ns) | 230 | 300 | 60 | 40 | 3 | 2 | 26 | 35 |
| $\mu$ (cm$^{-1}$) | 0.35 | 0.95 | 0.70 | 0.86 | 0.39 | 0.45 | 0.36 | 0.47 |
| $\Delta E/E$ (%) | 6.6 | 10.2 | 8.5 | 10.0 | 18 | 11.4 | 3.3 | 2.9 |
| Rel. light output (%) | 100 | 15 | 25 | 75 | 5 | 5 | 120 | 160 |

$LaCl_3$ and $LaBr_3$ have been reported on by van Loef at Delft University in the last 2 years [van Loef EVD, Dorenbos P, van Eijk C W E, Kramer K, Gudel H U, High-energy-resolution scintillator: Ce3+ activated LaCl3, Applied Physics Letters 77: 1467-1468, 2000; van Loef E V D, Dorenbos P, van Eijk C W E, Kramer K, Gudel H U, High-energyresolution scintillator: Ce3+ activated LaBr3. Applied Physics Letters 79: 1573-1575, 2001]. Table 1 shows that both scintillators have very fast decay time—faster than LSO, and very high light output—higher than NaI(T1). These properties lead to excellent timing and energy resolution for both Lanthanum Halide scintillators. The stopping power of $LaCl_3$ is similar to that of NaI(T1), while the stopping power of $LaBr_3$ is higher, making it the more ideal PET scintillator. On the other hand, the present inventors have shown that 3-D PET is not limited so much by its sensitivity, but rather by its count-rate capability. Clearly, both $LaCl_3$ and $LaBr_3$ would have higher count-rate capability than NaI(T1). The present inventors have performed simulation studies to compare a $LaBr_3$ scanner to the NaI(T1) C-PET and the GSO Allegro scanners, as well as systems based on LSO. In brief, these simulations indicate that a PET scanner using Lanthanum Halide scintillators can be designed with a geometry such that the count-rate capability is improved relative to current state-of-the-art scanners with other scintillators.

In addition to very high count-rate capability, the inventors also expect Lanthanum Halide scanners to have excellent energy resolution compared to PET scanners with other scintillators. For example, with $LaBr_3$, a total light output is expected to be more than double that of NaI(T1) (pulse clipped and normally integrated for 220 ns) and approximately five times that of GSO. The present inventors have performed additional simulations [Karp J S, Muehllehner G., Performance of a position-sensitive scintillation detector, Phys Med Biol 30: 643-655, 1985; Surti S, Karp J S, Freifelder R, Liu F., Optimizing the performance of a PET detector using discrete GSO crystals on a continuous light guide, IEEE Tran Nucl Sci 47: 1030-1036, 2000] to calculate position spectra for $LaBr_3$ crystals. The crystals are assumed to be 4×4×30 mm3 and the detector configured with a hexagonal arrangement of PMTs that are, for example, 39-mm diameter. It is also assumed that Anger-logic is used for positioning. The crystal separation that can be achieved with $LaBr_3$ has been found to be superior to pixelated Anger-logic NaI(T1) and GSO detectors due to higher light output of $LaBr_3$, which indicates that excellent image spatial resolution will be achieved for a PET scanner including these types of detectors.

Lanthanum Halide scintillators have been developed for application for single-photon imaging. Either scintillator can potentially improve the performance of a scintillation camera with as good or better stopping power than NaI(T1), and better energy resolution. The present inventors believe that the fast decay time makes these scintillators excellent candidates for PET imaging, as well—leapfrogging over GSO and LSO (in addition to NaI(T1) and BGO).

The high light output and fast decay time of the Lanthanum Halide scintillators opens the distinct possibility of measuring time-of-flight (TOF). Compared to conventional PET data, the measured data in TOF-PET contain more localized information about the distribution of activity. In conventional PET, there is no indication of where a pair of photons originated along the line-of-response (LOR) between a pair of detector elements, whereas in TOF-PET the point of annihilation is localized to a part of the LOR. As a result of the better localization in the TOF data, there is less amplification of noise in the reconstruction process, and better signal-to-noise in the reconstructed image. Instruments for TOF-PET and related reconstruction approaches were investigated intensively in the early 1980s [Ter-Pogossian M M, Mullani N A, et. al., Photon Time-of-Flight-Assisted Positron Emission Tomography, J. Comput. Assist. Tomog. 5: 227-239, 1981; Allemand R, Gresset C, Vacher J., Potential advantages of a Cesium Fluoride scintillator for a Time-of-Flight Positron Camera, J. Nucl. Med. 21: 153-155, 1980; Snyder D L, Thomas L J, Ter-Pogossian M M., A mathematical model for Positron Emission Tomography system having Time-of-Flight measurements, IEEE Tran Nucl Sci 28: 3575-3583, 1981; Tomitani T., Image reconstruction and noise evaluation in photon Time-of-Flight assisted Positron Emission Tomography, IEEE Trans. Nucl. Sci. 28: 4582-4589, 1981; Mullani N A, Wong W H, et. al., Preliminary results obtained with TOFPET-I—A whole-body Time-of-Flight Positron Emission Tomograph, J, Nucl, Med, 24: 11-12P, 1983; Philippe E A, Mullani N A, Some signal processing aspects of Time-of-Flight Positron Emission Tomography (TOFPET) system implementation, IEEE Trans. Nucl. Sci. 30: 715-719, 1983; M. Moszynski, Allemand R, et. al., Recent progress in fast timing with CsF scintillators in application to Time-of-Flight Positron Tomography in medicine, Nucl. Instru. Meth. 205: 239-249, 1983; Wong W H, Mullani N A, et. al., Image improvement and design optimization of the Time-of-Flight PET, J. Nucl. Med. 24: 52-60, 1983; Wong W H, Mullani NA, et. al., Performance Characteristics of the University of Texas TOFPET-I PET Camera, J. Nucl. Med. 25: 46-47P, 1984; M. Moszynski, Allemand R, et. al., Further study of scintillation counters with $BaF_2$ crystals for Time-of-Flight Positron Tomography in medicine, Nucl. Instru. Meth. A 226: 534-541, 1984]. The performance that was achievable at that time was limited by the available scintillator materials, since the crystals that were fast enough for TOF-PET, including $BaF_2$ and CsF had only low light output and poor energy resolution. With $BaF_2$, though, a time resolution of approximately 300 picosec could be achieved [Wong W H, Mullani N A, et. al., Characteristics of Small Barium Fluoride (BaF2) scintillator for high intrinsic resolution Time-of-Flight Positron Emission Tomography, IEEE Trans. Nucl. Sci. NS-31: 381-386, 1984]. A time resolution of 300 picosec leads to an uncertainty in position of 4.5 cm. At that time the main area of focus for PET was brain imaging—a much more difficult task for TOF due to the smaller diameter of the activity distribution, thus, a more challenging requirement for time resolution.

A more recent examination of TOF-PET was addressed by Moses and Derenzo in Moses W W, Derenzo S E, Prospects for time-of-flight PET using a LSO scintillator, IEEE Trans. Nucl. Sci. 46: 474-478, 1999. Here they measured timing resolution for LSO of 475 picosec for a crystal 30-mm in length. In principle, since $LaCl_3$ and $LaBr_3$ have higher light output and faster decay than LSO, the timing resolution should be better, as well. In fact, the present inventors have measured a timing resolution of 270 picosec for $LaBr_3$ for a 4×4×30 mm3 pixel and 310 picosec for an array of pixels coupled through a light guide to an array of PMTs. The present inventors have shown that with optimization of the crystal growth, careful design of the detector and choice of PMT, a very good timing resolution with pixelated $LaBr_3$ detectors may be achieved. The present inventors have set out to achieve a timing resolution good enough to warrant the addition of TOF information for image reconstruction.

Returning to a $LaBr_3$ based whole-body scanner with TOF capability, a timing resolution of 500 picosec would lead to a gain in SNR of 1.6 over a conventional PET tomograph for a 20-cm diameter cylinder [Budinger T F, Time-of-flight positron emission tomography: status relative to conventional PET, J. Nucl. Med. 24: 73-78, 1983]. Based on the simulated count-rate curves, the present inventors conclude that the effective count-rate of the $LaBr_3$-based whole-body scanner with an axial extent of 25 cm will be factor of 2.7 higher with TOF, reaching a peak noise-equivalent count-rate (NEC) of about 120 kcps×2.7=324 kcps, thus further distancing itself from the GSO-based Allegro scanner, which has a peak NEC of about 75 kcps. For a larger object with D=40 cm, more appropriate for a large patient, the SNR increase with TOF would be expected to be 2.3 with an NEC increase of 5.4. It is particularly beneficial that the TOF gain increases as the object size increases, since typically the NEC decreases for large patients due to increased attenuation and scatter. While these numbers may be optimistic, it is clear that the Lanthanum Halide scintillator has a significant potential advantage in SNR, if TOF is measured. Unlike other scintillators used in the early 1980's for TOF (e.g. $BaF_2$ and CsF), $LaBr_3$ has outstanding energy resolution and spatial resolution, as well. Thus, with $LaBr_3$ the designer would not need to trade one important aspect of imaging performance for another.

Even without the TOF benefit, a scanner based on LaBr3 would already have very competitive performance, resulting in a maximum NEC of 120 Kcps. At the clinical concentration obtained after injection of 10-15 mCi of FDG, resulting in a concentration of 0.1-0.2 uCi/cc, the NEC is expected to be between 80 and 110 Kcps. This is about a factor of 2 higher than currently achieved with the GSO-based Allegro scanner and LSO-based Accel scanner and a factor of 4-5 higher than achieved with a typical BGO scanner operated in 2-D mode. To put this benefit into perspective it is instructive to compare this benefit to the effort that would be necessary to achieve a comparable benefit with a non-time-of-flight scanner. Since the SNR is proportional to the square of the sensitivity, the relative sensitivity gain is Relative sensitivity=$D/\Delta x$, where D is the diameter of the object (patient), and $\Delta x$ is the positional uncertainty related to the time-of-flight uncertainty. For example, with a patient with a diameter of 40 cm, i.e. a heavy patient, and a time resolution of 500 picosec, the relative sensitivity gain is more than a factor of 5. To achieve the same result in a non-time-of-flight scanner would require increasing the axial FOV by more than a factor of 2. This implies more than twice the crystal material and twice the number of PMTs. Since the crystal and PMT cost is the dominant factor in the overall scanner cost, it can be seen that it would make a traditional PET scanner significantly more expensive to obtain the same benefit.

For heavy patients (e.g >250 lbs), the image quality of whole-body scans degrades using the conventional PET scanning techniques noted above. The promise of the $LaBr_3$ scanner is that high image quality will be achieved for very heavy patients, as well as average patients. For average patients, it is likely that counts can be traded for time to reduce overall scan time from 30 minutes to 5-15 minutes. The present invention is directed to the design of such a scanner to address these needs in the art.

SUMMARY OF THE INVENTION

The present invention relates to the design of a PET scanner based on Lanthanum Halide scintillators. The combination of very high light output and fast decay using the Lanthanum Halide scintillators further opens the possibility of time-of-flight with LaBr3, which will provide an additional gain in signal-to-noise ratio (SNR) and image quality. The low melting point of the Lanthanum Halide scintillators (similar to NaI(T1)) also leads to a potential benefit in cost effectiveness in the long run over scintillators (such as GSO and LSO) that have very high melting point (~2000° C.). Measurements show a 3.25% energy resolution (@662 keV) for a small sample (~1 $cm^2$) of $LaBr_3$ with a decay time of ~32 ns. An energy resolution of 511 keV of about 4% is achieved with pixels of 4×4×30 $mm^3$, a size suitable for PET imaging. Further, $LaBr_3$ has an excellent time resolution, due to its combination of fast rise time and high light output. Initial tests include a measurement of timing resolution of 240-350 ps, depending on the Cerium concentration of the $LaBr_3$ scintillator. These measurements are taken in coincidence with a BC-418 plastic scintillator. The energy and timing performance were optimized for a pixelated array of crystals packed into an Anger-logic detector. The resulting detector design is similar to that developed by the inventors previously for both GSO and NaI(T1) in that discrete crystals are coupled through a continuous light-guide to an array of close-packed photo-multiplier tubes. A pixelated detector is preferably used with at least one of these scintillators.

The fast rise time and high light output of the Lanthanum Halide scintillators opens the distinct possibility of measuring time-of-flight (TOF), which leads to less amplification of noise in the reconstruction process, and better signal-to-noise in the reconstructed image. Instruments for TOF-PET and related reconstruction approaches were investigated intensively in the early 1980s, but the performance that was achievable at that time was limited by the available scintillator materials, since the crystals that were fast enough for TOF-PET, including $BaF_2$ and CsF, had only low light output and poor energy resolution. A more recent examination of TOF-PET was addressed for LSO, measuring timing resolution from 300-475 ps depending on the size and shape of the crystal; the larger number corresponds to a crystal 30-mm in length. A timing resolution of 390 ps have been measured for a 4×4×30 $mm^3$ $LaCl_3$ crystal, and a 240-350 ps timing resolution has been measured for 4×4×30 $mm^3$ $LaBr_3$ pixels (depending on Cerium concentration). These results suggest that as good, or better results can be achieved with 30-mm long $LaBr_3$ crystals. The present inventors have recognized that, assuming a coincidence timing resolution $\Delta t=500$ ps, this infers an uncertainty in position $\Delta x$ of 7.5 cm, where $\Delta x=\Delta t/2c$. Based on early investigations on TOF, the present inventors argue that the gain in image signal-to-noise ratio is $(SNR)TOF=(D/\Delta x)^{1/2} (SNR)non-TOF$, where D is the diameter of the cylinder. For a $LaBr_3$ whole-body scanner with TOF capability, a timing resolution of 500 ps would lead to a SNR gain of 1.6 (NEC gain of 2.7) over a conventional PET tomograph for a 20-cm diameter object, and a SNR gain of 2.3 (NEC gain of 5.4) for a 40-cm diameter object.

Based on these considerations, the present invention relates to a PET scanner comprising a cavity for accepting a patient and a plurality of PET detector modules arranged in a cylindrical configuration about the cavity. Preferably, each PET detector includes a Lanthanum Halide scintillator comprising a plurality of Lanthanum Halide crystals, a light guide, and a plurality of photomultiplier tubes, where the Lanthanum Halide scintillator, the light guide and the photomultiplier tubes are arranged respectively peripherally (e.g., coaxially) about the cavity. The scanner circuitry is modified to include time-of-flight (TOF) processing that takes into account the timing and spatial resolution of the Lanthanum Halide scintillator so as to allow fast 3D processing for TOF.

BRIEF DESCRIPTION OF THE DRAWINGS

A Lanthanum Halide scintillator for three-dimensional time-of-flight PET in accordance with the invention is further described below with reference to the accompanying drawings, in which.

DETAILED DESCRIPTION OF THE INVENTION

The present invention relates to the development of a detector using Lanthanum Halide scintillators (for example $LaCl_3$ or $LaBr_3$) that will be applied to a 3D PET scanner with TOF capability. The resulting detector must have good sensitivity, good spatial resolution, good energy resolution, and good timing resolution. The good sensitivity is achieved by using thick crystals, e.g., about 30-mm thick, so that the efficiency for stopping 511 keV gamma rays is high. High sensitivity leads to more counts and/or shorter imaging time for a PET scanner. The good spatial resolution is achieved by using crystals with a small cross section, e.g., 4-mm by 4-mm. Good detector spatial resolution leads to high contrast and good definition of small structures in the image. The good energy resolution is achieved by using a scintillator with high light output, and both of the Lanthanum Halide scintillators have the highest light output of any known inorganic scintillator. Compared to NaI(Tl) (the gold standard) $LaCl_3$ is 1.2 times higher, and $LaBr_3$ is 1.6 times higher. Also, it is important that the detector design preserves the good energy resolution of the scintillator. The detector design in accordance with the invention uses a continuous optical coupling of the crystals to the PMTs, through the light-guide, thus leading to uniform collection of light. Whereas the energy resolution of a $4\times4\times30$ mm$^3$ pixel of $LaBr_3$ directly coupled to a PMT is 4% (FWHM=full width at half-maximum) at 511 keV, the energy resolution of an array of pixels coupled through a light guide to an array of PMTs is 5.5% at 511 keV, since some light is lost through the light guide. However, this is still an excellent result and will lead to very good scatter rejection in a PET scanner based on these detectors. Very good energy resolution and the use of a high energy threshold is needed to reduce scatter and random coincidences in PET imaging, which is particularly important for 3D imaging (no septa). Initial measurements of timing resolution with the same array of pixels coupled to a light guide and array of PMTs is 310-450 ps (depending on the Cerium concentration of the $LaBr_3$ scintillator. If the detector has 500 ps (or better) timing resolution, then TOF will have an important impact in improving the image quality (signal-to-noise) in the PET instrument.

Figure 5:
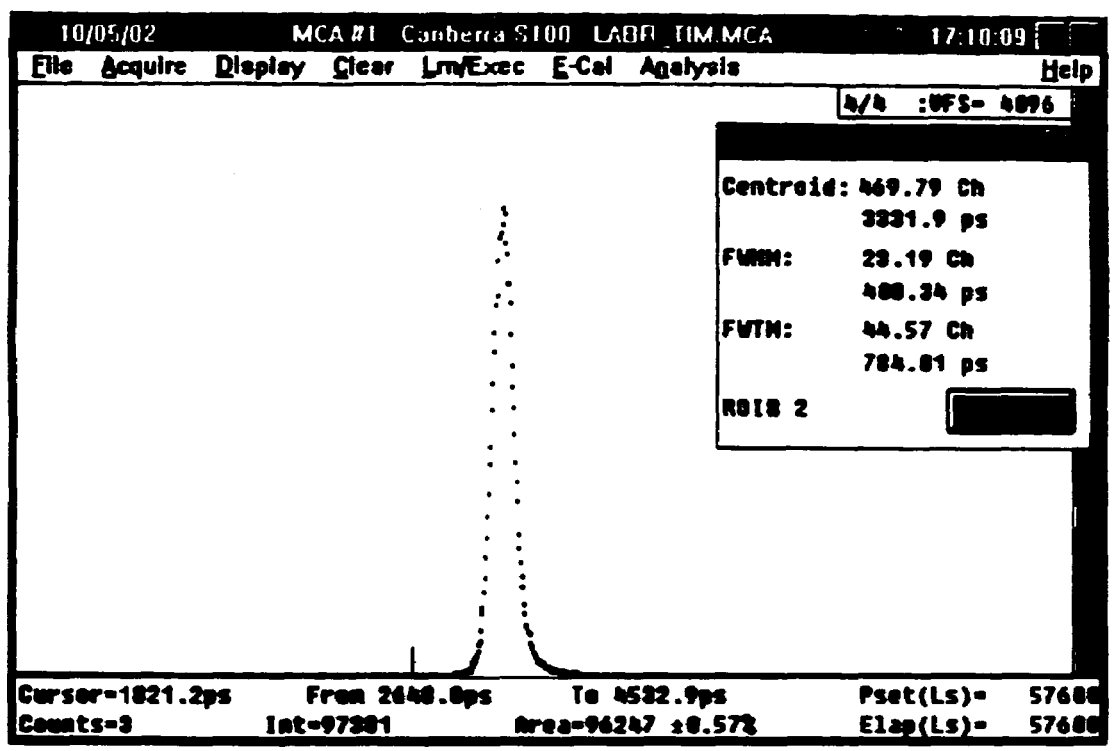
FIG. 5 illustrates the timing resolution results (FWHM=400 ps) for a single $10\times6$ mm$^2$ $LaBr_3$ crystal coupled to an XP2020 PMT in accordance with the invention, where PMT TTS=150 ps.

The present inventors have taken measurements of light output, energy resolution, and timing resolution of small samples of $LaCl_3$ and $LaBr_3$, pixels of $4\times4\times30$ mm$^3$, and arrays of pixels. To date, the inventors have taken measurements with 100-pixel arrays coupled to a light guide and an array of PMTs. The inventors have also performed computer simulations (Monte Carlo) which predict (and confirm) performance of the scintillators, in terms of energy, spatial, and timing resolution—for single crystals and for arrays of crystals in an Anger-logic detector. The inventors then designed a PET scanner and simulated the overall count-rate performance of the instrument and compared it to other PET scanners using other scintillators (such as the GSO Allegro scanner currently manufactured by Philips). Further, the present inventors have calculated the potential TOF improvement in terms of signal-to-noise (SNR) and noise-equivalent count-rate (NEC), as a function of timing resolution, and for different sized objects (e.g head vs. body). For example, FIG. 5 illustrates the timing resolution results (FWHM=400 ps) for a single $10\times6$ mm$^2$ $LaBr_3$ crystal coupled to an XP2020 PMT in accordance with the invention, where PMT TTS=150 ps.

The basic detector design is similar to that of a previous detector developed for GSO. This detector is described in a paper to Surti et al. entitled "Optimizing the Performance of a PET Detector Using Discrete GSO Crystals on a Continuous Light guide," IEEE Transactions on Nuclear Science, Vol. 47, NO. 3, June, 2000. GSO has higher stopping power than Lanthanum Halides (thus, a shorter crystal can be used), but it has lower light output (thus, worse energy resolution) and slower decay time (thus, worse timing resolution). In order to take full advantage of the better energy and timing resolution of Lanthanum Halides, the present inventors will need to modify the detector, including the light-guide and choice of PMTs. Also, the PET scanner design is based upon previous scanners (such as the GSO-based Allegro scanner from Philips), but the incorporation of TOF requires a re-design of the timing and processing electronics as noted below.

Recently, the present inventors developed pixelated NaI (T1) detectors for PET and believe that much of this development can be directly applied to $LaBr_3$ detectors whereby pixelated crystals on a continuous light-guide are coupled to a close-packed array of PMTs. In particular, the present inventors developed a detector consisting of NaI(T1) pixels of $4\times4\times30$ mm$^3$ in size with a 5-mm thick window, needed to seal the housing hermetically. The crystal length of 30 mm was chosen to attain a higher sensitivity than that of the C-PET whole-body scanner which uses a 25-mm thick continuous, Curve-Plate NaI(T1) detectors. The light-guide design choice and PMT size was based on our Monte Carlo detector simulations. Good crystal separation and energy resolution were maintained even at very short integration time. Based on these results, high quality pixelated detectors, using hygroscopic scintillators such as NaI(T1), is clearly feasible. Both Lanthanum Halide scintillators are also hygroscopic.

Figure 1:
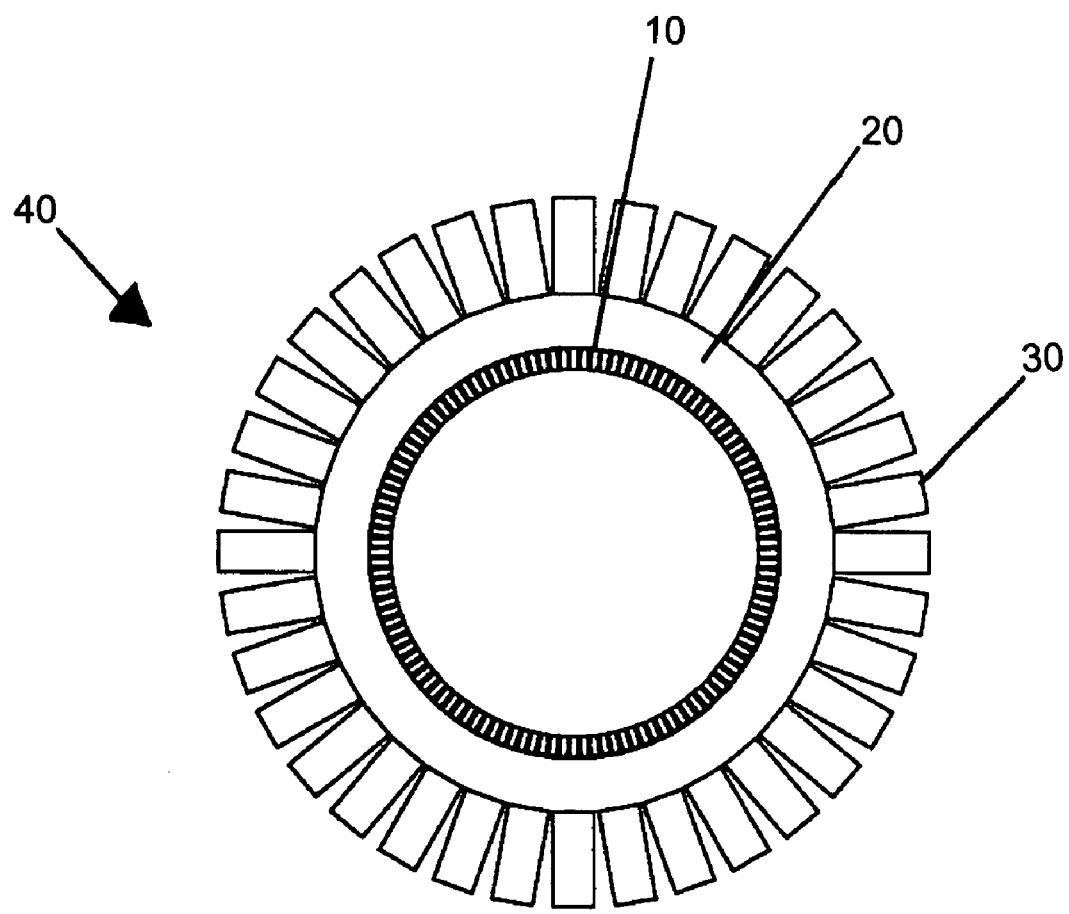
FIG. 1 illustrates an enlarged detector module formed in accordance with the invention so that a plurality of Lanthanum Halide scintillators (for example $LaCl_3$ or $LaBr_3$) are placed in a ring configuration with a light guide and a plurality of PMTs to form a PET detector.

The experimental results with detector modules and simulations of system performance led to the development of a proto-type scanner based upon these detectors, although a practical PET scanner with an LaBr₃ detector may use individual (flat) modules configured in a ring. As shown in FIG. 1, an enlarged detector module or PET scanner 40 was formed so that at least 28 modules (e.g., 36 modules) form a complete ring, with an axial extent of, e.g., 25 cm. The complete scanner 40 therefore is composed of 36,540 NaI (T1) pixels (crystals) 10 which are coupled to an optically continuous light-guide 20 and a hexagonal closed packed array of 39-mm diameter PMTs 30. The PET scanner 40 has a diameter of 92 cm and an axial field of view (AFOV) of 25 cm. Although this PET scanner 40 is not intended for production, initial tests demonstrate that higher count-rate performance and spatial resolution can be achieved with pixelated detectors instead of continuous Curve-Plate detectors. Moreover, the PET scanner 40 does not need to be a perfect cylinder with a perfectly circular cross-section as shown in FIG. 1. As noted above, a PET scanner in accordance with the invention may be constructed using individual flat modules configured in a ring. For example, 24 flat modules may be configured in a ring that is approximately cylindrical. Each module in such a configuration includes 1620 crystals, arranged 60×27.

Thus, the inventors have established the ability to use a hygroscopic material and have developed an effective manufacturing technique to make a large number of small crystals and construct a complete scanner with good crystal identification, i.e. good spatial resolution and good energy resolution. This experience is used to construct LaBr₃ pixelated detectors and a complete scanner system of the type shown in FIG. 2 based upon these detectors. The PET scanner system 50 illustrated in FIG. 2 includes standard electronic components for PET scanner systems except that, in accordance with the invention, the pre-amp/CFDs 60 and 70 include timing discriminators accurate to the timing resolution of the PET detectors and the coincidence logic board 80 is modified to record the timing information between the two pre-amp/CFDs and to output accurate time stamps signals (i.e., accurate to the timing resolution of the detectors) for the received gamma rays. As illustrated, the time stamp signals are passed through to the position processing unit 90 with the coincidence signals for the calculation of time-of-flight (TOF) of gamma rays through a patient in the cavity. The position processing unit 90 may then use the calculated TOF of gamma rays in the reconstruction of images of the patient.

As noted above, 3D PET imaging requires good energy resolution and a high lower energy gate to reduce scatter and randoms. Also, a fast scintillator and reduced light spread in the detector is needed to reduce dead time. As shown in Table 1 above, Lanthanum Halide scintillators meet these requirements.

Figure 2:
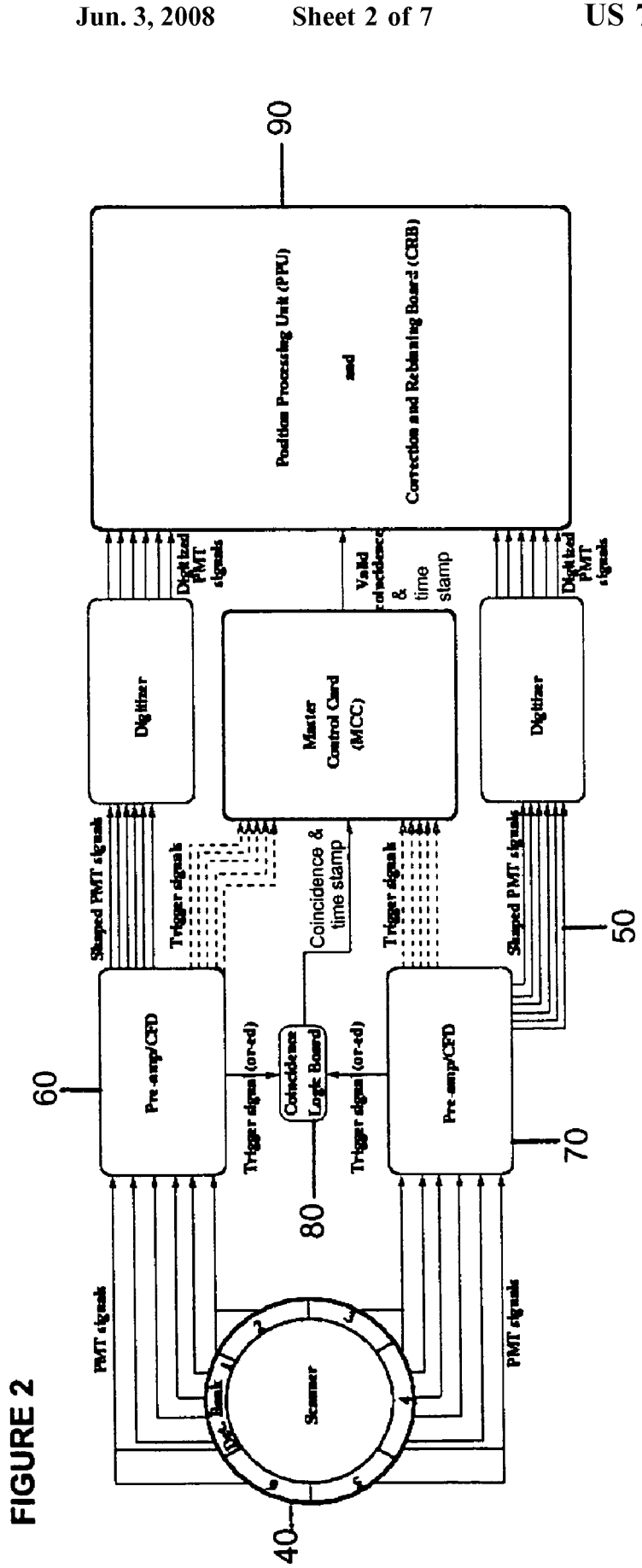
FIG. 2 illustrates a complete PET scanner with $LaBr_3$ pixelated detectors of the type shown in FIG. 1 as well as the associated electronics.
Figure 3:
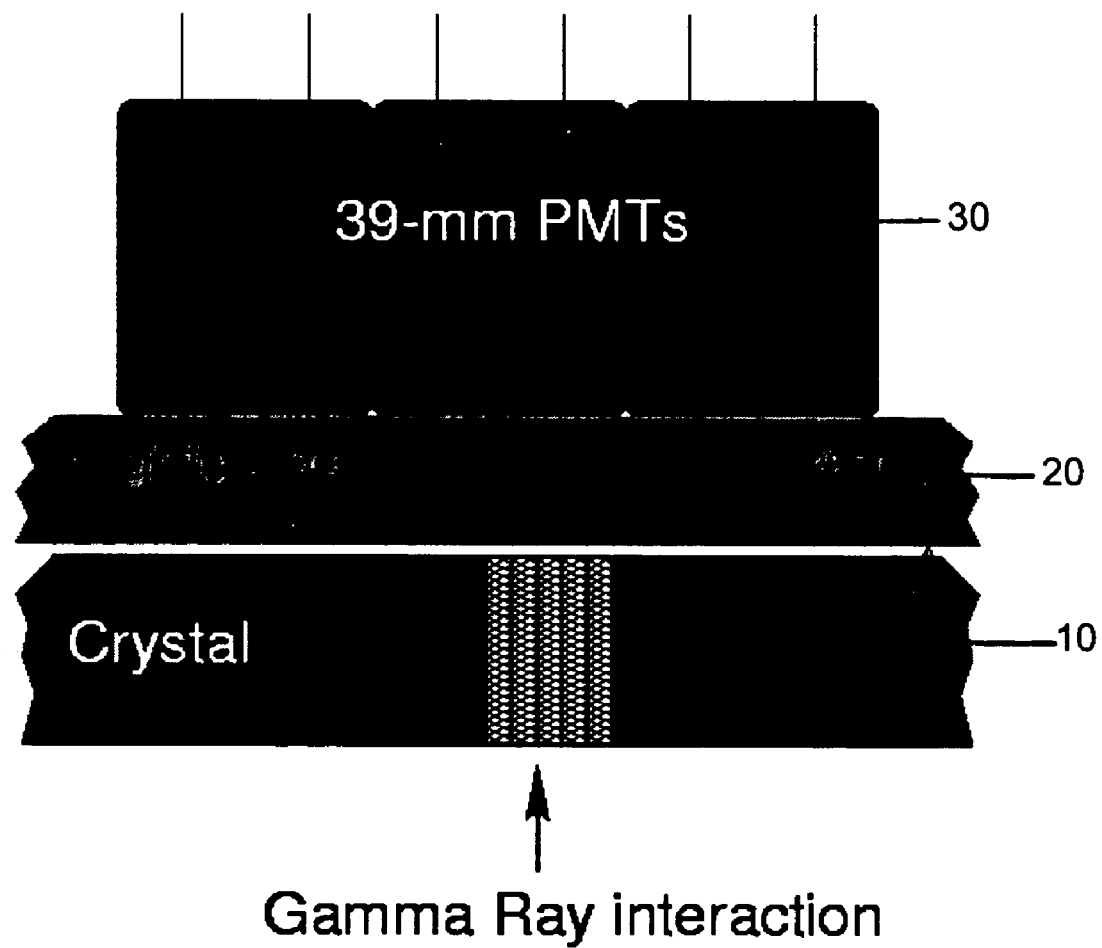
FIG. 3 illustrates a cross-section of a sample Anger-logic detector for crystal discrimination when using the Lanthanum Halide scintillators in a PET imaging device in accordance with the invention.
Figure 4:
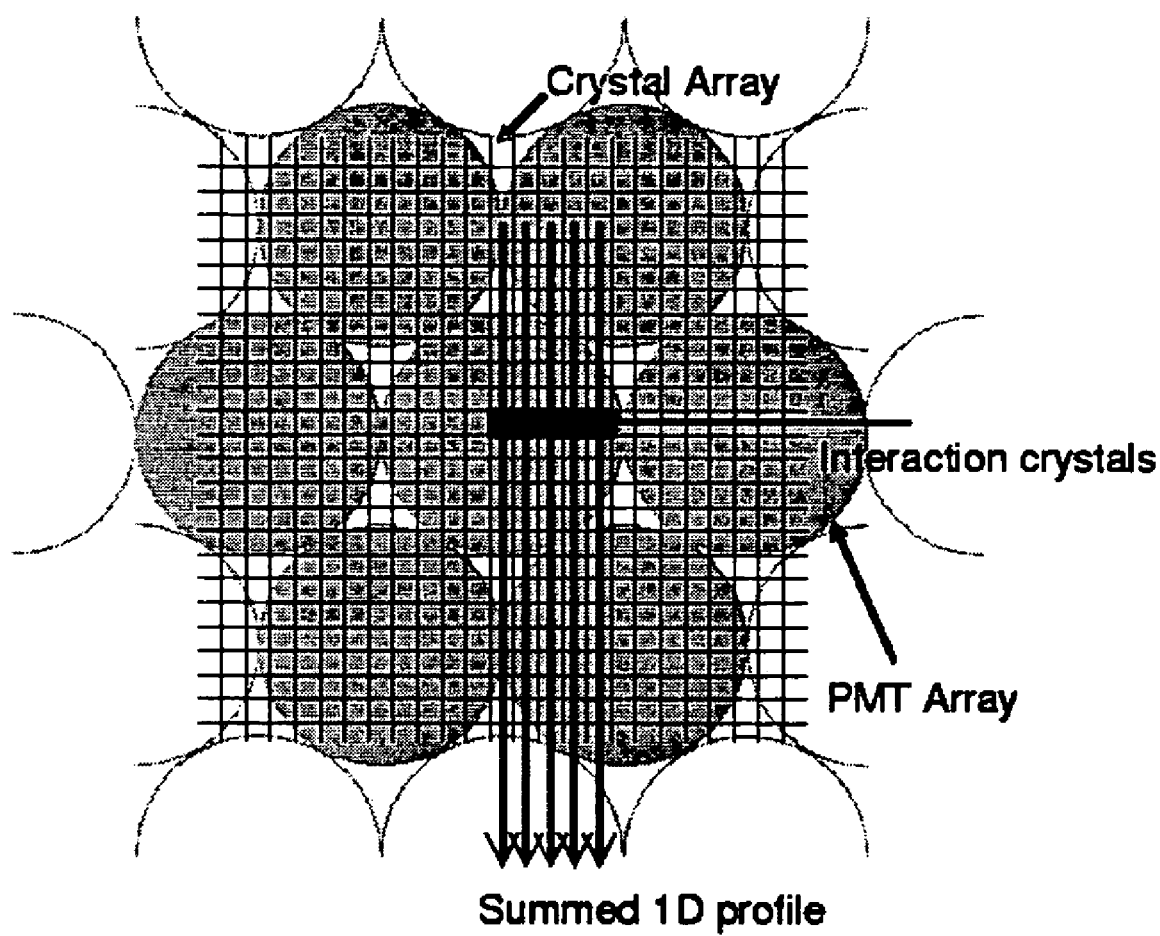
FIG. 4 illustrates a detector that uses a slotted light guide and 39 mm diameter PMTs in a hexagonal array for signal readout in accordance with the invention.

FIG. 3 illustrates a cross-section of a sample Anger-logic detector 40 for crystal discrimination when using the Lanthanum Halide scintillators in a PET imaging device of the type shown in FIGS. 1 and 2. The detector 40 is similar to a GSO Anger-logic detector that uses a slotted light guide and 39 mm diameter PMTs in a hexagonal array 50 as shown in FIG. 4 for signal readout. In this detector 40, light spread is restricted to a seven PMT cluster as shown in FIG. 4. A slotted light guide (as opposed to a non-slotted light guide) is not a requirement to make the Anger-logic detector work. Also, the PMTs 30 need not be 39-mm and the light guide need not be 23 mm thick; in fact, the present inventors are considering larger 50 mm PMTs since the complete system will therefore use fewer PMTs, thus reducing the cost.

Figure 6:
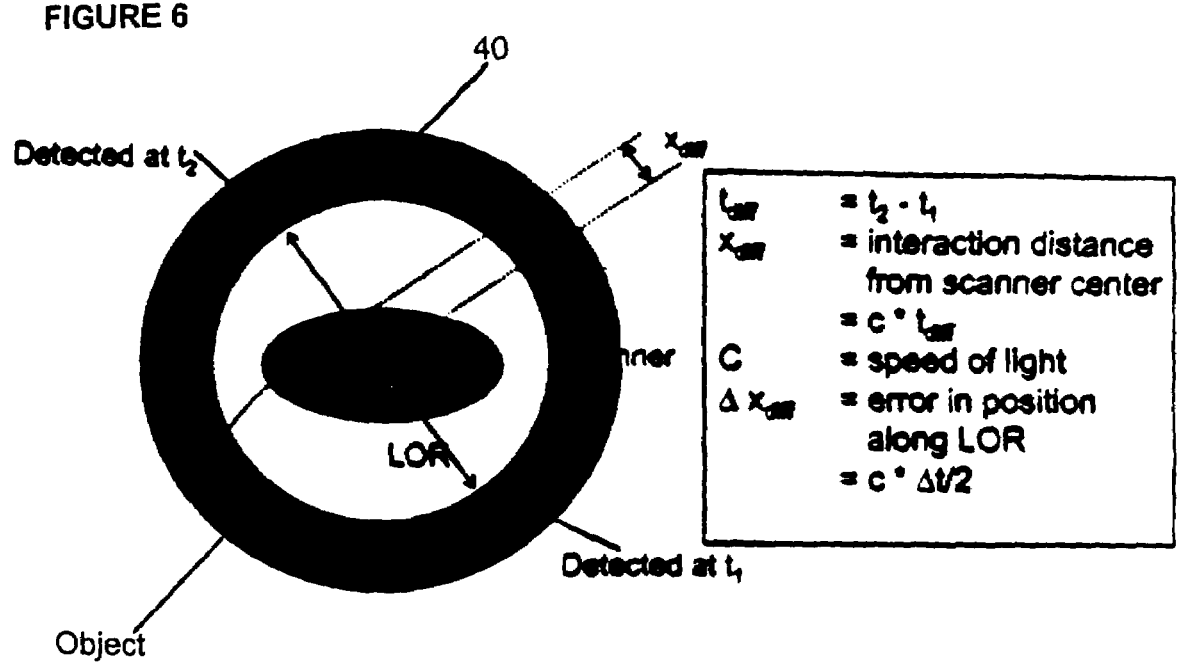
FIG. 6 generally illustrates a time-of-flight (TOF) scanner in accordance with the invention.

FIG. 6 generally illustrates a time-of-flight (TOF) scanner 40 based on the scanner design of FIGS. 1 and 2. As noted above, good timing resolution (Δt) provides the capability to measure the difference in arrival times ($t_{diff}$) of the coincident photons. Measurement of $t_{diff}$ localizes the distribution of activity along the measured line-of-response (LOR) leading to reduced amplification of noise in reconstruction, and improved image signal-to-noise ratio. In the past, it had been shown that $$SNR_{TOF} = (D/\Delta X_{diff})^{1/2} \times SNR_{non-TOF}$$

where, SNR=Image pixel Signal-to-Noise ratio and D=object diameter. Similarly it can be shown that:

$$NEC_{TOF} = (D/\Delta X_{diff}) \times NEC_{non-TOF}$$

Figure 7:
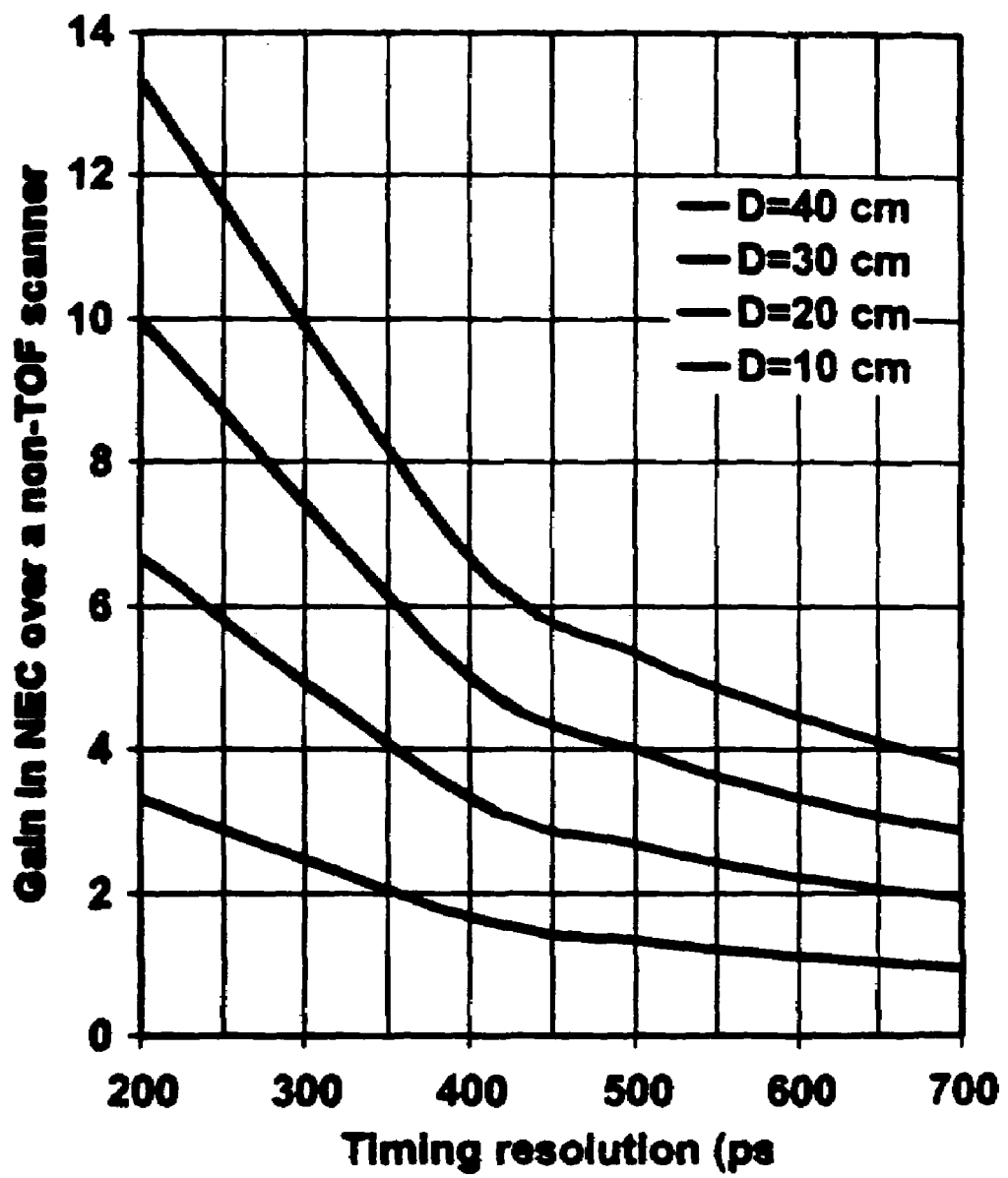
FIG. 7 illustrates the gain in the NEC as a function of timing resolution and diameter of the object being imaged when using a TOF La-Halide scanner in accordance with the invention.

Based on timing resolution of 440-450 ps for Anger-logic detectors (simulations), the inventors used Δt=500 ps→$\Delta x_{diff}$=7.5 cm. As shown in FIG. 7, the result is a factor of 2.67 and 5.33 increase in the peak NEC rates for the 20 and 40-cm diameter cylinders.

Thus, the present invention relates to a PET imaging system that incorporates Lanthanum Halide scintillators having excellent energy resolution, light output and timing properties that can be incorporated in a high performance 3D whole-body scanner that can lead to significant increase in NEC rates for heavy patients over the current generation of scanners.

The excellent timing resolution can be maintained at less than 450 ps in an Anger-logic detector using 4×4×30 mm³ crystals. A time-of-flight PET scanner using these scintillators can potentially lead to another factor of five increase in the peak NEC rate for heavy patients.

Although exemplary implementations of the invention have been described in detail above, those skilled in the art will readily appreciate that many additional modifications are possible in the exemplary embodiments without materially departing from the novel teachings and advantages of the invention. For example, the present inventors have recently performed timing resolution measurements of two LaBr₃ arrays in coincidence and have measured 340 ps-600 ps, depending on the Cerium concentration. The higher Cerium concentration leads to better timing resolution, due to its faster rise time and comparable light output. A PET scanner based on these scintillator arrays would be expected to achieve similar results. The faster Lanthanum Halide scintillator (higher Cerium concentration) with 340 ps coincidence timing is more desirable; however, time-of-flight measurements would prove useful even with Lanthanum Halide scintillators with 600 ps coincidence timing resolution. Accordingly, any such modifications are intended to be included within the scope of this invention as defined by the following exemplary claims.

We claim:
1. A PET scanning system comprising:
a PET scanner comprising a cavity for accepting a patient and a plurality of PET detector modules arranged about said cavity, each PET detector including a LaBr₃ or LaCl₃ scintillator comprising a plurality of LaBr₃ or LaCl₃ crystals, respectively, and said scintillator having a decay time constant τ≦35 ns and a light output at least equal to the light output of NaI(T1), and a plurality of photomultiplier tubes arranged with respect to said plurality of scintillator crystals wherein each photomultiplier tube receives light output from several of said scintillator crystals and wherein said scintillator crystals and said photomultiplier tubes are arranged respectively peripherally around said cavity;

a time stamp circuit that records the time of receipt of gamma rays by respective PET detectors and provides timing data outputs; and a processor that receives said timing data outputs, calculates time-of-flight (TOF) of gamma rays through a patient in the cavity, and uses said TOF of gamma rays in the reconstruction of images of the patient.

2. A PET detector scanning system as in claim 1, wherein said scintillator crystals are about 30 mm thick.

3. A PET scanning system as in claim 1, wherein said scintillator crystals have cross-sections of approximately 4 mm by 4 mm.

4. A PET scanning system as in claim 1, wherein said scintillator crystals are connected to said photomultiplier tubes through a light guide using optical coupling.

5. A PET scanning system as in claim 1, wherein said plurality of PET detector modules are arranged in an approximately cylindrical configuration about said cavity.

* * * * *

UNITED STATES PATENT AND TRADEMARK OFFICE
CERTIFICATE OF CORRECTION

| | |
|---|---|
| PATENT NO. | : 7,381,958 B2 |
| APPLICATION NO. | : 10/706799 |
| DATED | : June 3, 2008 |
| INVENTOR(S) | : Joel S. Karp et al. |

Page 1 of 1

It is certified that error appears in the above-identified patent and that said Letters Patent is hereby corrected as shown below:

In the Specification

Column 1,
On Line 12, after the Heading "Government Support", please delete the entire paragraph:
"The present invention was supported by the U.S. Department of Energy under Grant No. DOE DE-FG02-88ER60642 and by the National Institutes of Health under NIH Grant No. 1-R21-EB-001684-01. The government may have certain rights in the invention."

And insert the following:
-- This invention was made with government support under EB001684 awarded by the National Institutes of Health and DE-FG02-88ER60642 awarded by the Department of Energy. The government has certain rights in the invention. --.

Signed and Sealed this
Seventh Day of December, 2021

Drew Hirshfeld
*Performing the Functions and Duties of the
Under Secretary of Commerce for Intellectual Property and
Director of the United States Patent and Trademark Office*